(12) United States Patent
Moloney

(10) Patent No.: US 10,426,502 B2
(45) Date of Patent: Oct. 1, 2019

(54) NOSEBLEED-ATTENUATING APPARATUS

(71) Applicant: Jill Jackson Moloney, Fort Collins, CO (US)

(72) Inventor: Jill Jackson Moloney, Fort Collins, CO (US)

(*) Notice: Subject to any disclaimer, the term of this patent is extended or adjusted under 35 U.S.C. 154(b) by 484 days.

(21) Appl. No.: 14/742,451

(22) Filed: Jun. 17, 2015

(65) Prior Publication Data

US 2016/0367276 A1 Dec. 22, 2016

(51) Int. Cl.
*A61B 17/24* (2006.01)
*A61F 13/38* (2006.01)
*A61F 13/12* (2006.01)

(52) U.S. Cl.
CPC ............ *A61B 17/24* (2013.01); *A61F 13/126* (2013.01); *A61F 13/38* (2013.01)

(58) Field of Classification Search
CPC ......... A61B 17/24; A61B 17/26; A61B 17/12; A61B 17/12022; A61B 17/12104; A61B 17/12099; A61B 17/12131; A61B 17/12159; A61B 17/083; A61B 2017/242; A61B 2017/246; A61B 2017/248; A61B 2017/12004; A61B 17/244; A61F 13/126; A61F 13/38; A61F 13/2002; A61F 13/2005; A61F 13/2022; A61F 13/204; A61F 2013/00476; A61F 2013/00463; A61F 2013/00468; A61F 2/18; A61F 2/186; A61F 5/005; A61F 5/00; A61F 5/001; A61F 5/002; A61F 5/003; A61F 5/004; A61F 5/006; A61F 5/007; A61F 5/008; A61F 13/20; A61F 13/2008; A61F 13/2011; A61F 13/2017; A61F 13/202; A61F 13/26; A61F 13/263; A61F 13/266; A61F 13/36; A61F 13/385; A61F 2013/2014; A61F 15/005; A61F 5/30; A61F 5/32; A61F 5/34; A61F 5/08; A61F 5/56; A61F 5/566;

(Continued)

(56) References Cited

U.S. PATENT DOCUMENTS 3,228,392 A * 1/1966 Speyer ............... A61H 23/0218
601/108
3,675,652 A * 7/1972 McPherson ........... A61M 31/00
604/1

(Continued)

FOREIGN PATENT DOCUMENTS

CN 20255402 11/2012

OTHER PUBLICATIONS

Acep. Focus on: Treatment of Epistaxis, article by Gilman. Website, http://www.acep.org, originally downloaded Jul. 6, 2015, 3 pages total.

(Continued)

*Primary Examiner* — Katherine H Schwiker
(74) *Attorney, Agent, or Firm* — Craig R. Miles; CR Miles P.C.

(57) ABSTRACT

A nosebleed-attenuating apparatus including a pressure applicator configured to engage with an external bodily surface proximate an area of nasal vascularization between a nose and an upper lip; and a pressure receiver coupled to the pressure applicator, the pressure receiver configured to receive pressure; whereby an amount of the pressure is transferred to the pressure applicator for application to the external bodily surface.

14 Claims, 4 Drawing Sheets

(58) Field of Classification Search
CPC ........ A61M 35/006; A61M 2210/0618; A61M 31/00; A61M 35/00; A61M 35/003; A61M 15/08; A61M 15/085
USPC .............. 606/201, 204.45, 202–203, 204.15, 606/204.25, 204.35, 204.55; 604/514, 604/289, 303, 1–3, 11–18, 285, 286
See application file for complete search history.

(56) References Cited

U.S. PATENT DOCUMENTS

| | | | | |
|---|---|---|---|---|
| 3,905,335 A * | 9/1975 | Kapp | ..................... | A62B 23/06 128/206.11 |
| 4,306,555 A * | 12/1981 | Ritter | ..................... | A61F 13/38 19/145.3 |
| 4,457,756 A | 7/1984 | Kern et al. | | |
| 4,646,739 A | 3/1987 | Doyle | | |
| 4,820,266 A | 4/1989 | Berry | | |
| 5,342,388 A * | 8/1994 | Toller | ................... | A61B 17/132 601/134 |
| 5,383,891 A | 1/1995 | Walker | | |
| 5,584,822 A * | 12/1996 | Lively | .............. | A61B 17/12104 604/285 |
| 5,895,409 A * | 4/1999 | Mehdizadeh | .............. | A61F 5/08 606/199 |
| 5,899,918 A | 5/1999 | Knott et al. | | |
| 6,709,443 B1 | 3/2004 | Rix | | |
| 6,971,388 B1 * | 12/2005 | Michaels | ................... | A61F 5/08 128/204.12 |
| 7,390,331 B2 * | 6/2008 | Santin | ....................... | A61F 5/08 606/199 |
| 7,909,845 B2 | 3/2011 | Ashenhurst | | |
| 8,231,648 B2 | 7/2012 | Rix | | |
| 9,782,289 B1 * | 10/2017 | Rastegar | ................... | A61F 5/56 |
| 9,855,054 B1 * | 1/2018 | Stcyr | ................... | A61B 17/132 |
| 2003/0028214 A1 * | 2/2003 | Benz | ................... | A61B 17/132 606/201 |
| 2003/0229375 A1 * | 12/2003 | Fleischer | ........... | A61B 17/1325 606/201 |
| 2004/0194788 A1 | 10/2004 | Sweet | | |
| 2005/0288620 A1 * | 12/2005 | Shippert | ............. | A61F 13/2005 604/11 |
| 2006/0229664 A1 * | 10/2006 | Finkielsztein | ......... | A61B 17/12 606/201 |
| 2006/0266360 A1 * | 11/2006 | Noce | ....................... | A61F 5/08 128/206.11 |
| 2008/0178873 A1 * | 7/2008 | Alpers | ...................... | A61F 5/08 128/200.24 |
| 2009/0007919 A1 * | 1/2009 | Dolezal | ................. | A61M 15/08 128/206.11 |
| 2009/0093840 A1 * | 4/2009 | MacDonald | .............. | A61F 5/08 606/199 |
| 2011/0270290 A1 * | 11/2011 | Nadam | ................... | A61F 13/38 606/162 |
| 2012/0046607 A1 * | 2/2012 | Syk | ......................... | A61F 11/08 604/103.02 |
| 2013/0081637 A1 * | 4/2013 | Foley | ....................... | A61F 5/08 128/848 |
| 2013/0184684 A1 * | 7/2013 | Yardley | ................. | A61F 13/126 604/514 |
| 2013/0274794 A1 * | 10/2013 | Chalfoun | ............... | A61B 17/12 606/201 |
| 2016/0030720 A1 * | 2/2016 | Husain | .................. | A61M 31/00 604/514 |

OTHER PUBLICATIONS

American Academy of Otolaryngology. Nosebleeds. Website, http://www.entnet.org, originally downloaded Jul. 6, 2015, 4 pages total.
American Rhinologic Society. Epistaxis (Nosebleeds), article by Suh et al. Website, http://care.american-rhinologic.org, originally downloaded Jul. 6, 2015, 3 pages total.
Books.mcgraw-hill.com. Clinical Correlation, Epistaxis. Website, http://books.mcgraw-hill.com, originally downloaded Jul. 6, 2015, 2 pages total.
Encyclopedia.com. Nosebleed, article by Franz et al. Website, http://www.encyclopedia.com, originally downloaded Jul. 6, 2015, 3 pages total.
Fatakia, et al. Epistaxis: A Common Problem. The Ochsner Journal, 2010 Fall; 10(3); 4 pages total.
Guthrie, K. Epistaxis, Case Study. Website, http://lifeinthefastlane.com, originally downloaded Jul. 6, 2015, 12 pages total.
Wikihow.Com. How to Stop a Nosebleed in Seconds by Putting Paper Under Your Upper Lip. Website, http://www.wikihow.com, originally downloaded Jul. 6, 2015, 2 pages total.

* cited by examiner

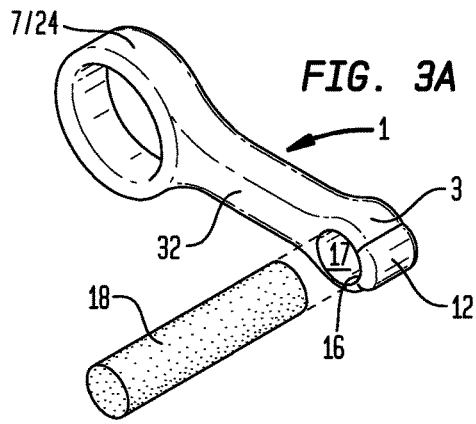
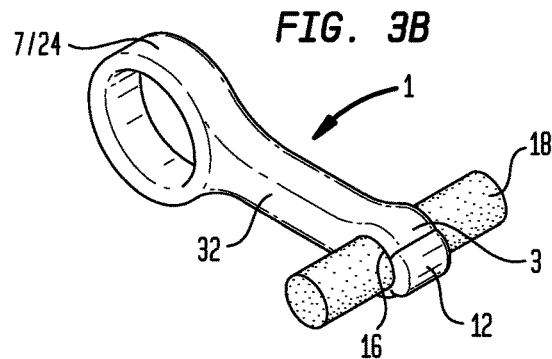
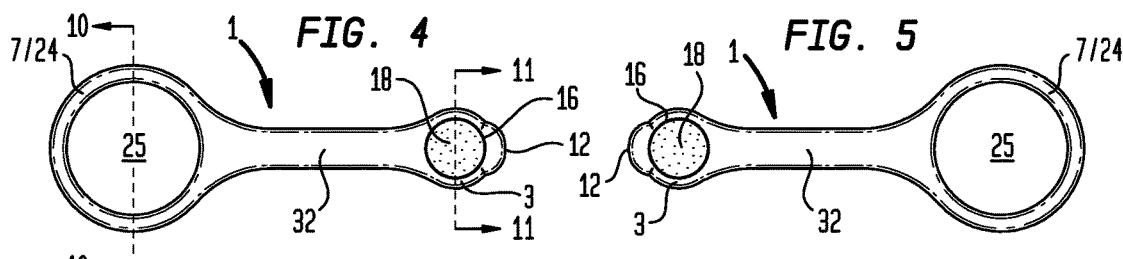
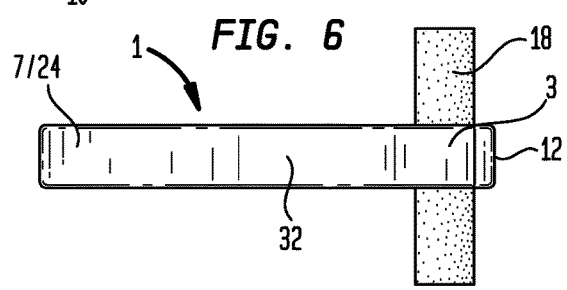
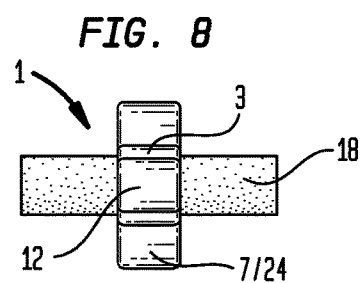
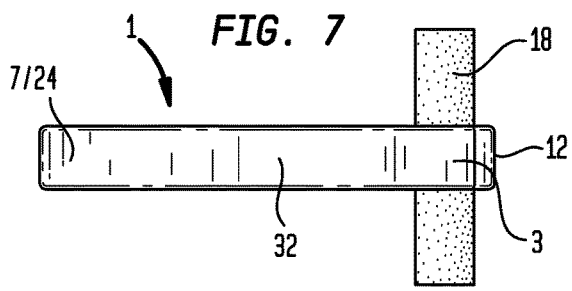
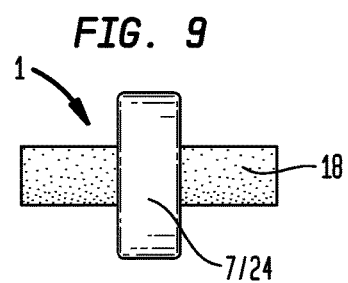
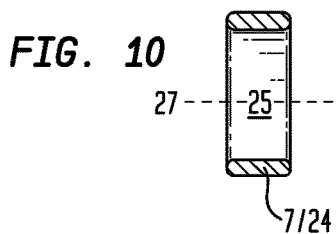
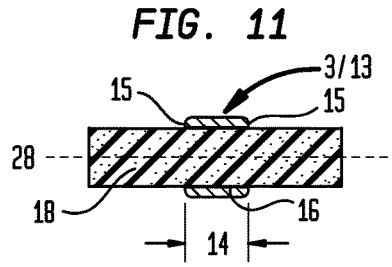

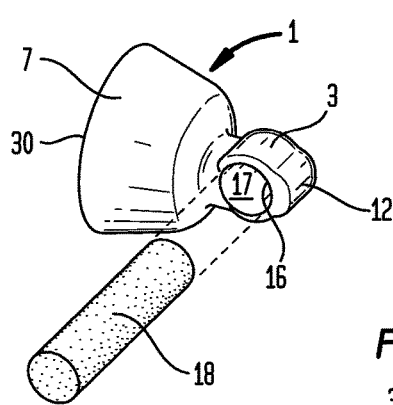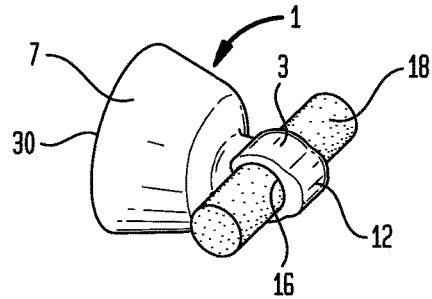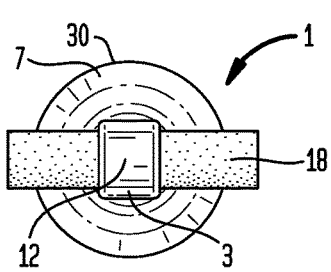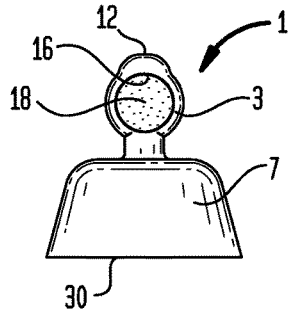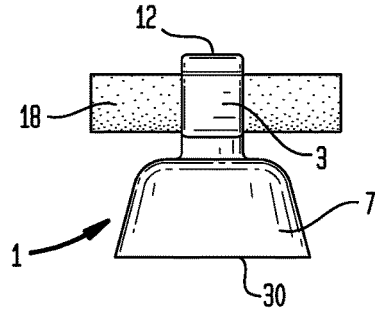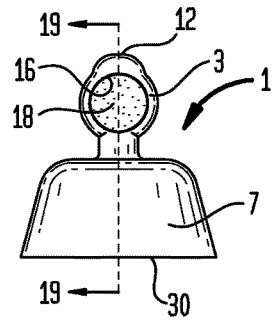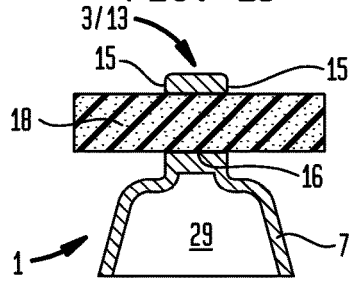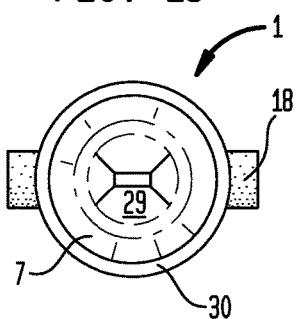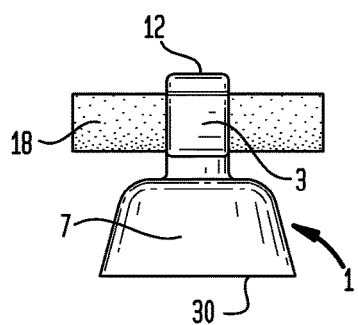

US 10,426,502 B2

NOSEBLEED-ATTENUATING APPARATUS

I. FIELD OF THE INVENTION

The present invention relates, in general, to the treatment of epistaxis (bleeding from the nose) or the alleviation of one or more symptoms of epistaxis. More particularly, the present invention relates to a nosebleed-attenuating apparatus and methods of making and using the same.

II. SUMMARY OF THE INVENTION

A broad object of a particular embodiment of the invention can be to provide a nosebleed-attenuating apparatus including a pressure applicator configured to engage with an external bodily surface proximate an area of nasal vascularization between a nose and an upper lip; and a pressure receiver coupled to the pressure applicator, the pressure receiver configured to receive pressure; whereby an amount of the pressure is transferred to the pressure applicator for application to the external bodily surface.

Another broad object of a particular embodiment of the invention can be to provide a method of making a nosebleed-attenuating apparatus, the method including providing a pressure applicator configured to engage with an external bodily surface proximate an area of nasal vascularization between a nose and an upper lip; and coupling a pressure receiver to the pressure applicator, the pressure receiver configured to receive pressure; whereby an amount of the pressure is transferred to the pressure applicator for application to the external bodily surface.

Another broad object of a particular embodiment of the invention can be to provide a method of using a nosebleed-attenuating apparatus to attenuate a nosebleed, the method including obtaining the nosebleed-attenuating apparatus as described above; engaging the pressure applicator with the external bodily surface; and applying pressure to the pressure receiver. Subsequently, an amount of pressure is transferred to the pressure applicator and correspondingly, to the external bodily surface proximate the area of nasal vascularization, whereby the amount of pressure is sufficient to attenuate a nosebleed.

Naturally, further objects of the invention are disclosed throughout other areas of the specification, drawings, and claims.

III. BRIEF DESCRIPTION OF THE DRAWINGS

FIG. 3A is a perspective view of a particular embodiment of the nosebleed-attenuating apparatus, whereby an absorbent element is exploded out of an aperture element opening which is defined by an aperture element disposed in a pressure applicator.

FIG. 3B is a perspective view of the particular embodiment of the nosebleed-attenuating apparatus shown in FIG. 3A, whereby the absorbent element is received within the aperture element opening.

FIG. 4 is a first side view of a particular embodiment of the nosebleed-attenuating apparatus.

FIG. 5 is a second side view of a particular embodiment of the nosebleed-attenuating apparatus.

FIG. 6 is a top plan view of a particular embodiment of the nosebleed-attenuating apparatus.

FIG. 7 is a bottom plan view of a particular embodiment of the nosebleed-attenuating apparatus.

FIG. 8 is a first end view of a particular embodiment of the nosebleed-attenuating apparatus.

FIG. 9 is a second end view of a particular embodiment of the nosebleed-attenuating apparatus.

FIG. 10 is a cross sectional view 10-10 of the particular embodiment of the nosebleed-attenuating apparatus shown in FIG. 4.

FIG. 11 is a cross sectional view 11-11 of the particular embodiment of the nosebleed-attenuating apparatus shown in FIG. 4.

FIG. 12A is a perspective view of a particular embodiment of the nosebleed-attenuating apparatus, whereby an absorbent element is exploded out of an aperture element opening which is defined by an aperture element disposed in a pressure applicator.

FIG. 12B is a perspective view of the particular embodiment of the nosebleed-attenuating apparatus shown in FIG. 12A, whereby the absorbent element is received within the aperture element opening.

FIG. 13 is a first side view of a particular embodiment of the nosebleed-attenuating apparatus.

FIG. 14 is a second side view of a particular embodiment of the nosebleed-attenuating apparatus.

FIG. 15 is a first end view of a particular embodiment of the nosebleed-attenuating apparatus.

FIG. 16 is a second end view of a particular embodiment of the nosebleed-attenuating apparatus.

FIG. 17 is a top plan view of a particular embodiment of the nosebleed-attenuating apparatus.

FIG. 18 is a bottom plan view of a particular embodiment of the nosebleed-attenuating apparatus.

FIG. 19 is a cross sectional view 19-19 of the particular embodiment of the nosebleed-attenuating apparatus shown in FIG. 14.

IV. DETAILED DESCRIPTION OF THE INVENTION

Figure 1:
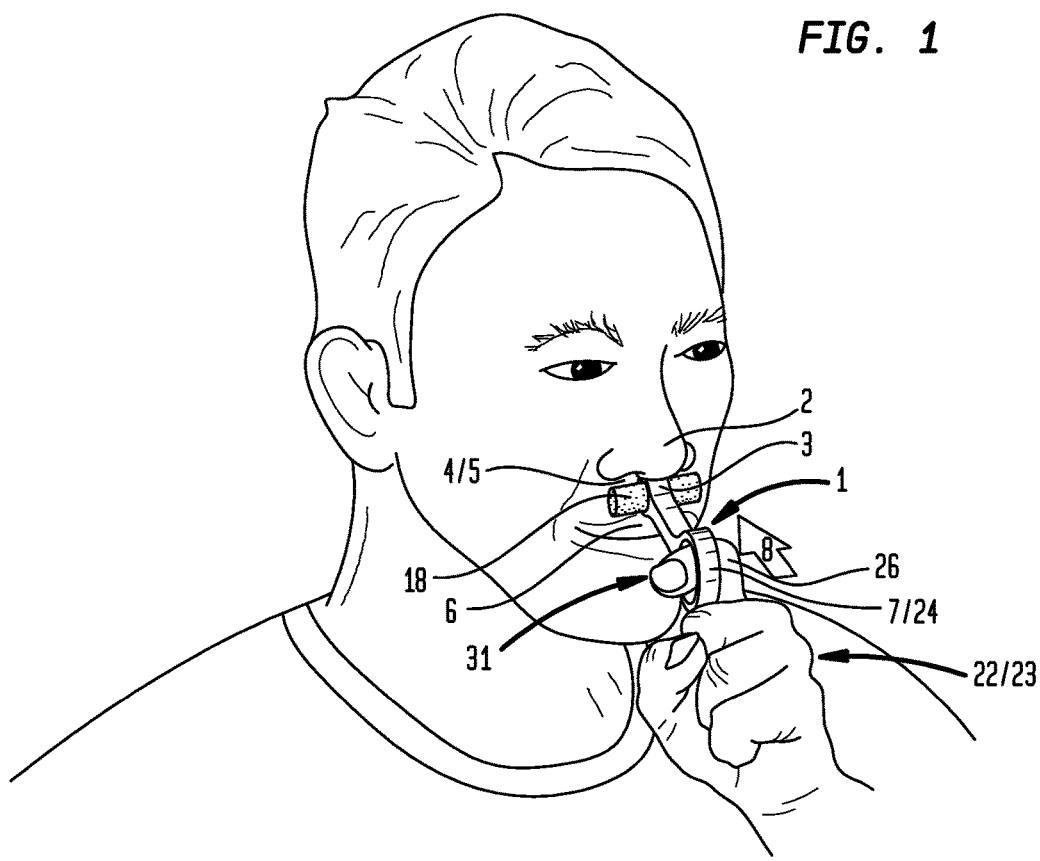
FIG. 1 is an illustration of a method of using a particular embodiment of a nosebleed-attenuating apparatus.

Now referring primarily to FIG. 1, which illustrates a method of using a nosebleed-attenuating apparatus (1) to attenuate epistaxis or bleeding from the nose (2), whereby the nosebleed-attenuating apparatus (1) includes a pressure applicator (3) configured to engage with an external bodily surface (4) proximate an area of nasal vascularization (5) between the nose (2) and an upper lip (6), and a pressure receiver (7) coupled to the pressure applicator (3). The pressure receiver (7) is configured to receive pressure (8), whereby an amount of the pressure (8) is transferred to the pressure applicator (3) for application to the external bodily surface (4). The method of using the nosebleed-attenuating apparatus (1) includes engaging the pressure applicator (3) with the external bodily surface (4) and applying pressure (8) to the pressure receiver (7). Subsequently, an amount of the pressure (8) is transferred to the pressure applicator (3) and correspondingly, to the external bodily surface (4) proximate the area of nasal vascularization (5), whereby the amount of pressure (8) is sufficient to attenuate a nosebleed.

For the purposes of this invention, the term "attenuate" means reduce or lessen the severity of. For example, attenuating a nosebleed means reducing or lessening the severity of bleeding from the nose to treat the nosebleed or alleviate one or more symptoms of the nosebleed.

Figure 2:
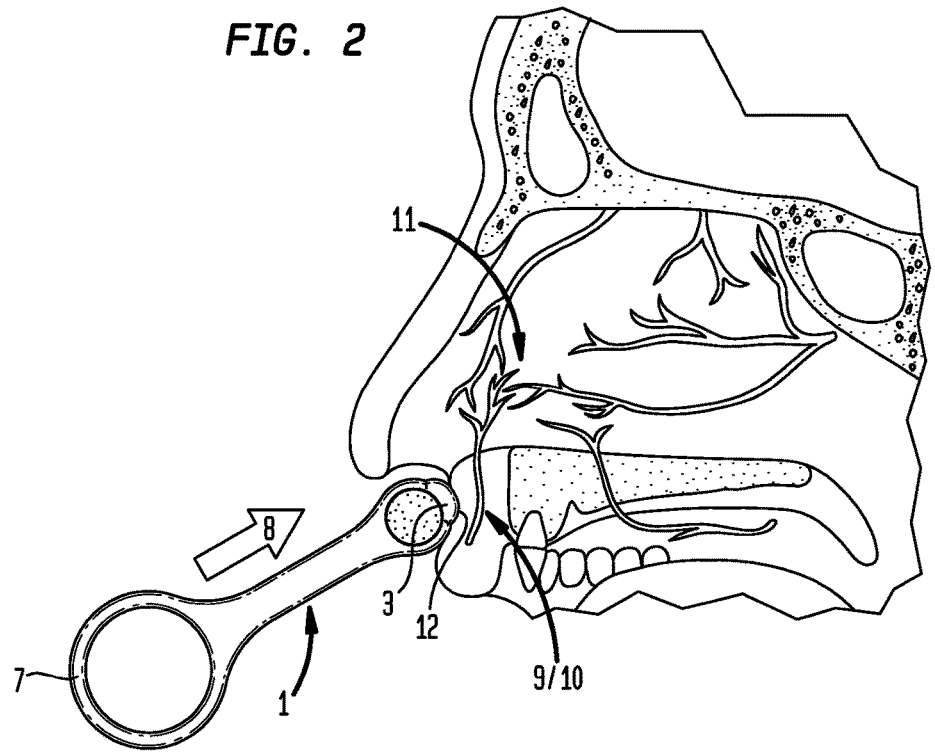
FIG. 2 is an illustration of a method of using a particular embodiment of a nosebleed-attenuating apparatus, whereby the illustration details a plurality of arteries which supply blood to the nose.

Now referring primarily to FIG. 2, the nosebleed-attenuating apparatus (1) includes a pressure applicator (3) configured to engage with an external bodily surface (4) proximate an area of nasal vascularization (5) between a nose (2) and an upper lip (6). As to particular embodiments, the area of nasal vascularization (5) includes a portion of a superior labial artery (9), for example a septal branch (10) of the superior labial artery (9).

The application of pressure (8) to the septal branch (10) of the superior labial artery (9) can decrease or preclude blood flow to Kiesselbach's plexus, which lies in Kiesselbach's area (11) (also known as Kiesselbach's triangle or Little's area). Kiesselbach's plexus is a region in the anteroinferior part of the nasal septum where a plurality of arteries anastomose to form a vascular plexus, whereby one of the arteries is the septal branch (10) of the superior labial artery (9). As about ninety percent of nosebleeds occur in Kiesselbach's area (11), there is a substantial advantage in decreasing or precluding blood flow to this area to attenuate a nosebleed.

The pressure applicator (3) can have any of a numerous and wide variety of configurations of varying dimensions such that an engagement surface (12) of the pressure applicator (3) can adjacently engage with the external bodily surface (4) to apply pressure (8), whereby the application of pressure (8) to the external bodily surface (4) can compress the area of nasal vascularization (5) between the nose (2) and the upper lip (6), constricting the septal branch (10) of the superior labial artery (9) to attenuate a nosebleed.

As but one illustrative example, the pressure applicator (3) can be configured as a cylinder (13) having a cylinder length (14) disposed between opposing cylinder ends (15) (as shown in the example of FIG. 11 and FIG. 19). As to particular embodiments, a portion of a perimeter of the cylinder (13) can define an arcuate engagement surface (12) which can engage with the external bodily surface (4) when the nosebleed-attenuating device (1) is used to attenuate a nosebleed. As to this particular embodiment, the arcuate engagement surface (12) can be contiguous with the perimeter of the cylinder (13).

As to other particular embodiments having a pressure applicator (3) with a generally cylindrical configuration, the engagement surface (12) of the pressure applicator (3) can outwardly extend from a portion of the perimeter of the cylinder (13) (as shown in the examples of the Figures).

Now referring primarily to FIG. 3A, FIG. 3B, FIG. 4, FIG. 5, FIG. 11, FIG. 12A, FIG. 12B, FIG. 13, FIG. 14, and FIG. 19, the pressure applicator (3) can, but need not necessarily, further include an aperture element (16) disposed within the pressure applicator (3), whereby the aperture element (16) defines an aperture element opening (17) which communicates between the opposing cylinder ends (15).

Again referring primarily to FIG. 3A, FIG. 3B, FIG. 4, FIG. 5, FIG. 11, FIG. 12A, FIG. 12B, FIG. 13, FIG. 14, and FIG. 19, the aperture element (16) can define an aperture element opening (17) configured to receive an absorbent element (18), which may be useful to absorb fluid, such as blood, flowing from the nose (2) during a nosebleed.

Now referring primarily to FIG. 4, FIG. 5, FIG. 13, and FIG. 14, as but one illustrative example, the aperture element (16) can define an aperture element opening (17) having a generally circular cross section configured to receive an absorbent element (18) having a corresponding generally circular cross section.

Now referring primarily to FIG. 3A through FIG. 9 and FIG. 11 through FIG. 19, the nosebleed-attenuating apparatus (1) can, but need not necessarily, further include the absorbent element (18) capable of receipt within the aperture element opening (17).

The absorbent element (18) can be formed from any of a numerous and wide variety of materials capable of absorbing fluid, such as blood. For example, the absorbent element (18) can be formed from natural or synthetic materials, including, as non-limiting examples: bamboo, cotton, gauze, hemp, paper, paper-like products, plastic, plastic-like products, polyester, or the like, or combinations thereof.

Additionally, as to particular embodiments, the absorbent element (18) can be formed from one or more materials which are washable, allowing the absorbent element (18) to be washed and reused. In contrast, as to other particular embodiments, the absorbent element (18) can be formed from one or more materials which are disposable.

Figure 20A:
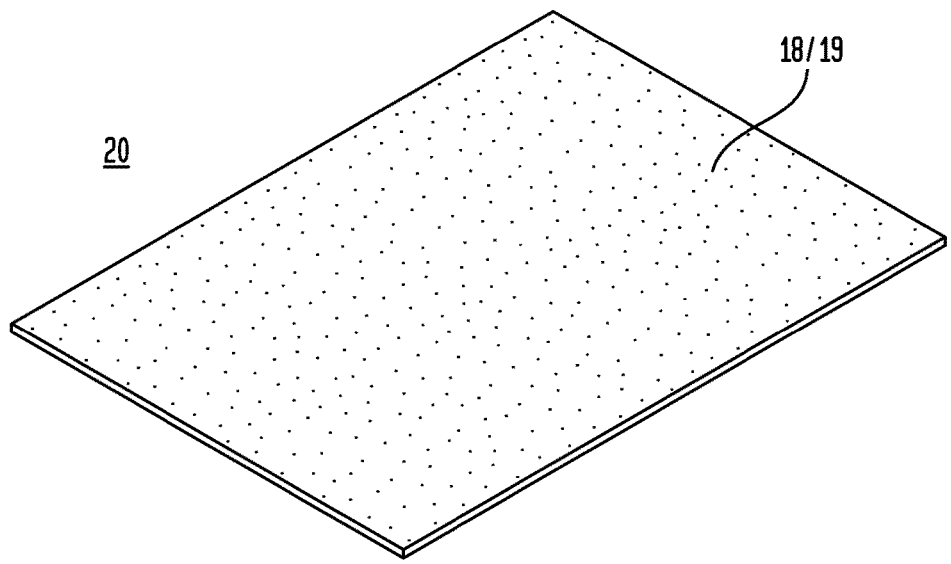
FIG. 20A is a perspective view of an absorbent element of a particular embodiment of the nosebleed-attenuating apparatus, whereby the absorbent element comprises an adjustable absorbent element configured in a first configuration.
Figure 20B:
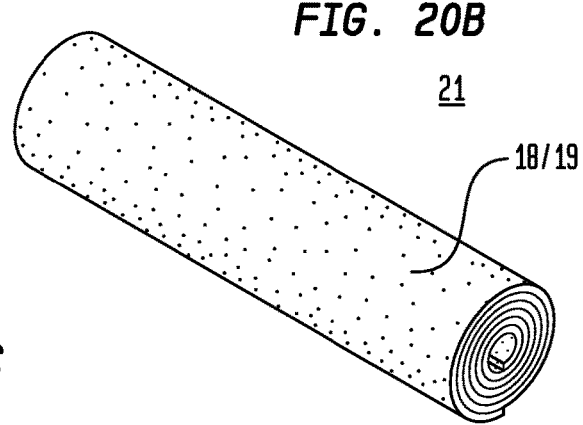
FIG. 20B is a perspective view of the absorbent element shown in FIG. 20A, whereby the absorbent element is configured in a second configuration.
Figure 20C:
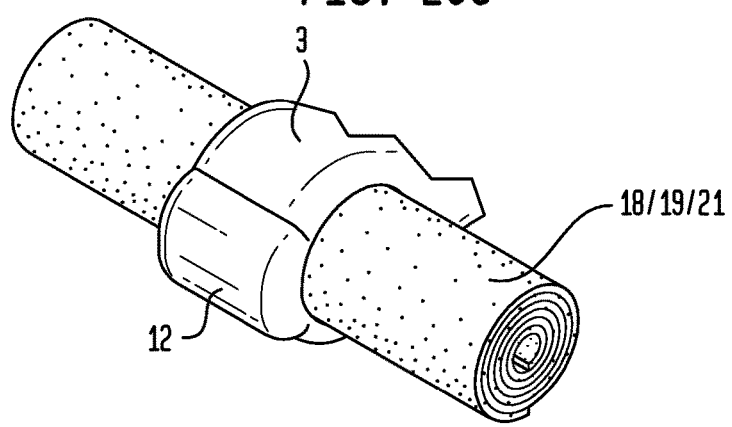
FIG. 20C is a perspective view of the absorbent element shown in FIG. 20B, whereby the absorbent element is received within an aperture element opening of a pressure applicator.

Now referring primarily to FIG. 20A through FIG. 20C, as to particular embodiments, the absorbent element (18) can be configured as an adjustable absorbent element (19) capable of adjustment between first and second configurations (20) (21), whereby in the second configuration (21), the adjustable absorbent element (19) has a generally circular cross section which facilitates receipt within the aperture element opening (17). As but one illustrative example, the adjustable absorbent element (19) can have a first configuration (20) in which the adjustable absorbent element (19) is substantially planar. Upon collapsing, for example by rolling, the second configuration (21) can be achieved.

Now referring primarily to FIG. 3A through FIG. 10 and FIG. 12A through FIG. 19, the nosebleed-attenuating apparatus (1) further includes a pressure receiver (7) coupled to the pressure applicator (3). The pressure receiver (7) is configured to receive pressure (8), whereby an amount of the pressure (8) is transferred to the pressure applicator (3) for application to the external bodily surface (4) proximate the area of nasal vascularization (5) between the nose (2) and the upper lip (6).

The pressure receiver (7) can have any of a numerous and wide variety of configurations of varying dimensions, whereby the pressure receiver (7) is capable of receiving pressure (8) from a pressure generator (22), whereby an amount of the pressure (8) is transferred to the pressure applicator (3).

Again referring primarily to FIG. 3A through FIG. 10 and FIG. 12A through FIG. 19, as to particular embodiments, the pressure receiver (7) can be configured as a grippable pressure receiver (7) which can be gripped by a portion of a hand (23) of a pressure generator (22).

Now referring primarily to FIG. 3A through FIG. 10, as to particular embodiments, the grippable pressure receiver (7) can include an annular member (24) which defines an annular member opening (25) configured to receive at least one finger (26) of a hand (23) of a pressure generator (22). As to these particular embodiments, the annular member (24) can define an annular member opening (25) which has a generally circular cross section configured to receive the at least one finger (26).

Now referring primarily to FIG. 4, FIG. 10, and FIG. 11, as to particular embodiments, the nosebleed-attenuating apparatus (1) can be configured to have an annular member opening longitudinal axis (27) of the annular member opening (25) which disposes in generally parallel relation to an aperture element opening longitudinal axis (28) of the aperture element opening (17). However, the invention need not be limited to this configuration.

Now referring primarily to FIG. 12A through FIG. 19, as to other particular embodiments, the grippable pressure receiver (7) can define a receptacle (29) having a receptacle open end (30) disposed in opposing relation to the pressure applicator (3), whereby the receptacle (29) can be configured to receive at least one fingertip portion (31) of a hand (23) of a pressure generator (22). As to these particular embodiments, the grippable pressure receiver (7) can define a receptacle (29) which has a generally circular cross section configured to receive the at least one fingertip portion (31).

Now referring primarily to FIG. 3A through FIG. 7, the nosebleed-attenuating apparatus (1) can, but need not necessarily, further include an elongate member (32) disposed between the pressure applicator (3) and the pressure receiver (7). As to particular embodiments, the elongate member (32) may be useful to provide a distance between the pressure applicator (3) and the pressure receiver (7).

A method of making the nosebleed-attenuating apparatus (1) includes providing a pressure applicator (3) configured to engage with an external bodily surface (4) proximate an area of nasal vascularization (5) between a nose (2) and an upper lip (6); and coupling a pressure receiver (7) to the pressure applicator (3), whereby the pressure receiver (7) is configured to receive pressure (8). Subsequently, an amount of the pressure (8) is transferred to the pressure applicator (3) for application to the external bodily surface (4). As to particular embodiments, the area of nasal vascularization (5) includes a portion of a superior labial artery (9), for example a septal branch (10) of the superior labial artery (9).

The method of making the nosebleed-attenuating apparatus (1) can, but need not necessarily, further include configuring the pressure applicator (3) as a cylinder (13) having a cylinder length (14) disposed between opposing cylinder ends (15).

The method of making the nosebleed-attenuating apparatus (1) can, but need not necessarily, further include configuring a portion of a perimeter of the cylinder (13) to define an arcuate engagement surface (12) of the pressure applicator (3), whereby the arcuate engagement surface (12) is contiguous with the perimeter of the cylinder (13).

As to other particular embodiments, the method of making the nosebleed-attenuating apparatus (1) can, but need not necessarily, further include outwardly extending an arcuate engagement surface (12) of the pressure applicator (3) from a portion of a perimeter of the cylinder (15).

The method of making the nosebleed-attenuating apparatus (1) can, but need not necessarily, further include disposing an aperture element (16) within the cylinder (13), whereby the aperture element (16) defines an aperture element opening (17) which communicates between the opposing cylinder ends (15). As to particular embodiments, the method can, but need not necessarily, further include configuring the aperture element opening (17) to receive an absorbent element (18). As to particular embodiments, the method can, but need not necessarily, further include configuring the aperture element (18) to define an aperture element opening (17) which has a generally circular cross section configured to receive an absorbent element (18) having a corresponding generally circular cross section.

The method of making the nosebleed-attenuating apparatus (1) can, but need not necessarily, further include providing the absorbent element (18) capable of receipt within the aperture element opening (17). As to particular embodiments, the method can, but need not necessarily, further include forming the absorbent element (18) from washable material. As to other particular embodiments, the method can, but need not necessarily, further include forming the absorbent element (18) from disposable material.

The method of making the nosebleed-attenuating apparatus (1) can, but need not necessarily, further include configuring the pressure receiver (7) as a grippable pressure receiver (7) capable of being gripped by a portion of a hand (23) of a pressure generator (22).

As to particular embodiments, the method of making the nosebleed-attenuating apparatus (1) can, but need not necessarily, further include configuring the grippable pressure receiver (7) as an annular member (24). The method can, but need not necessarily, further include configuring the annular member (24) to define an annular member opening (25) configured to receive at least one finger (26) of a hand (23) of a pressure generator (22). The method can, but need not necessarily, further include configuring the annular member (24) to define an annular member opening (25) which has a generally circular cross section. The method can, but need not necessarily, further include disposing an annular member opening longitudinal axis (27) of the annular member opening (25) in generally parallel relation to an aperture element opening longitudinal axis (28) of the aperture element opening (17).

As to other particular embodiments, the method of making the nosebleed-attenuating apparatus (1) can, but need not necessarily, further include configuring the grippable pressure receiver (7) to define a receptacle (29) having a receptacle open end (30) disposed in opposing relation to the pressure applicator (3), whereby the receptacle (29) is configured to receive at least one fingertip portion (31) of a hand (23) of a pressure generator (22). The method can, but need not necessarily, further include configuring the grippable pressure receiver (7) to define the receptacle (29) which has a generally circular cross section.

The method of making the nosebleed-attenuating apparatus (1) can, but need not necessarily, further include disposing an elongate member (32) between the pressure applicator (3) and the pressure receiver (7).

The nosebleed-attenuating apparatus (1) or components of the nosebleed-attenuating apparatus (1) can be formed from any of a numerous and wide variety of materials including, as non-limiting examples: metal, metal alloys, wood, polymeric material, plastic, plastic-like material, acrylic, acrylonitrile butadiene styrene (ABS), nylon, polycarbonate, polyamide, polyester, polypropylene, polyvinyl chloride-based materials, silicone-based materials, or the like, or combinations thereof. As to particular embodiments, the nosebleed-attenuating apparatus (1) or components of the nosebleed-attenuating apparatus (1) can be formed from a material which is sterilizable or capable of maintaining functionality following any of a numerous and wide variety of sterilization processes.

The nosebleed-attenuating apparatus (1) or components of the nosebleed-attenuating apparatus (1) can be produced from any of a numerous and wide variety of processes including, as non-limiting examples: press molding, injection molding, fabrication, machining, printing, additive printing, or the like, or combinations thereof.

As to particular embodiments, the nosebleed-attenuating apparatus (1) can be formed as a one-piece construct (as shown in the examples of the Figures).

As to other particular embodiments, the nosebleed-attenuating apparatus (1) can be formed from a plurality of pieces which can be assembled into an embodiment of the nosebleed-attenuating apparatus (1).

A method of using the nosebleed-attenuating apparatus (1) include obtaining the nosebleed-attenuating apparatus (1) configured as described above, engaging the pressure applicator (3) with the external bodily surface (4) and applying pressure (8) to the pressure receiver (7). Subsequently, an amount of the pressure (8) is transferred to the pressure applicator (3) and correspondingly, to the external bodily surface (4) proximate the area of nasal vascularization (5), whereby the amount of pressure (8) is sufficient to attenuate a nosebleed. As to particular embodiments, the area of nasal vascularization (5) includes a portion of a superior labial artery (9), for example a septal branch (10) of the superior labial artery (9).

As to particular embodiments, the amount of pressure (8) can be sufficient to constrict the septal branch (10) of the superior labial artery (9) to attenuate the nosebleed.

As to particular embodiments, the amount of pressure (8) can be sufficient to attenuate the nosebleed within a time period of less than about 60 seconds.

As to particular embodiments, attenuating the nosebleed can alleviate one or more symptoms of epistaxis.

As to particular embodiments, attenuating the nosebleed can treat epistaxis.

The method of using the nosebleed-attenuating apparatus (1) can, but need not necessarily, further include inserting an absorbent element (18) into an aperture element opening (17) defined by an aperture element (16) disposed within the pressure applicator (3).

The method of using the nosebleed-attenuating apparatus (1) can, but need not necessarily, further include disposing the absorbent element (18) received within the aperture element opening (17) beneath the nose (2) to absorb fluid, such as blood, flowing from the nose (2) during a nosebleed.

As can be easily understood from the foregoing, the basic concepts of the present invention may be embodied in a variety of ways. The invention involves numerous and varied embodiments of a nosebleed-attenuating apparatus and methods for making and using such nosebleed-attenuating apparatuses, including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "door stop" should be understood to encompass disclosure of the act of "attenuating"— whether explicitly discussed or not—and, conversely, were there effectively disclosure of the act of "attenuating", such a disclosure should be understood to encompass disclosure of an "attenuator" and even a "means for attenuating". Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the nosebleed-attenuating apparatuses herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application, if any, provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:

1. A nosebleed-attenuating apparatus comprising:
   a cylinder defining an aperture element opening extending between a first cylinder end and an opposing second cylinder end, said cylinder sized to fit between a nose and an upper lip;
   an annular member coupled to said cylinder, said annular member defining an annular member opening configured to receive at least one finger of a hand to apply pressure to said annular member;
   wherein an annular member opening longitudinal axis of said annular member is parallel to an aperture element opening longitudinal axis of said aperture element opening; and
   a single straight elongate member extending between said annular member and said cylinder, said elongate member being directly coupled to said annular member and said cylinder;
   a cylindrical absorbent element comprising a first absorbent portion and a second absorbent portion, said absorbent element positioned in said aperture element opening such that said first absorbent portion extends out of said first cylinder end and said second absorbent portion extends out of said second cylinder end;
   wherein said nosebleed-attenuating apparatus is symmetrical about a central axis passing through said cylinder, said annular member, and said elongate member;
   wherein during use, said pressure is transferred from said annular member to said cylinder for application to an external surface of a body to compress an area of nasal vascularization between said nose and said upper lip; and
   wherein during said use, an entirety of said nosebleed-attenuating apparatus remains outside of said body.

2. The nosebleed-attenuating apparatus of claim 1, wherein said cylinder comprises a continuous cylinder length between said first and second cylinder ends.

3. The nosebleed-attenuating apparatus of claim 1, wherein a portion of a perimeter of said cylinder defines an arcuate engagement surface which is contiguous with said perimeter of said cylinder.

4. The nosebleed-attenuating apparatus of claim 1, wherein an arcuate engagement surface outwardly extends from a perimeter of said cylinder, said arcuate engagement surface and said cylinder formed as a one-piece construct.

5. The nosebleed-attenuating apparatus of claim 1, wherein said aperture element opening comprises a circular cross section.

6. A nosebleed-attenuating apparatus comprising:
   a cylinder defining an aperture element opening extending between a first cylinder end and an opposing second cylinder end, said cylinder sized to fit between a nose and an upper lip; and
   a receptacle coupled to said cylinder at a center of a receptacle closed end, said receptacle having a receptacle open end opposite said receptacle closed end, said receptacle open end configured to receive at least one fingertip portion of a hand to apply pressure to said receptacle;
   wherein said receptacle open end is open in a direction opposite said cylinder;
   a cylindrical absorbent element comprising a first absorbent portion and a second absorbent portion, said absorbent element positioned in said aperture element opening such that said first absorbent portion extends out of said first cylinder end and said second absorbent portion extends out of said second cylinder end;
   wherein said nosebleed-attenuating apparatus is symmetrical about a central axis passing through said cylinder and said receptacle;
   wherein during use, said pressure is transferred from said receptacle to said cylinder for application to an external surface of a body to compress an area of nasal vascularization between said nose and said upper lip; and
   wherein during said use, an entirety of said nosebleed-attenuating apparatus remains outside of said body.

7. The nosebleed-attenuating apparatus of claim 6, wherein said cylinder comprises a continuous cylinder length between said first and second cylinder ends.

8. The nosebleed-attenuating apparatus of claim 6, wherein a portion of a perimeter of said cylinder defines an arcuate engagement surface which is contiguous with said perimeter of said cylinder.

9. The nosebleed-attenuating apparatus of claim 6, wherein an arcuate engagement surface outwardly extends from a perimeter of said cylinder, said arcuate engagement surface and said cylinder formed as a one-piece construct.

10. The nosebleed-attenuating apparatus of claim 6, wherein said aperture element opening comprises a circular cross section.

11. A method of attenuating a nosebleed, said method comprising:
    obtaining a nosebleed-attenuating apparatus comprising:

a cylinder defining an aperture element opening extending between a first cylinder end and an opposing second cylinder end, said cylinder sized to fit between a nose and an upper lip;

an annular member coupled to said cylinder, said annular member defining an annular member opening configured to receive at least one finger of a hand to apply pressure to said annular member;

wherein an annular member opening longitudinal axis of said annular member is parallel to an aperture element opening longitudinal axis of said aperture element opening; and a single straight elongate member extending between said annular member and said cylinder, said elongate member being directly coupled to said annular member and said cylinder;

a cylindrical absorbent element comprising a first absorbent portion and a second absorbent portion, said absorbent element positioned in said aperture element opening such that said first absorbent portion extends out of said first cylinder end and said second absorbent portion extends out of said second cylinder end;

wherein said nosebleed-attenuating apparatus is symmetrical about a central axis passing through said cylinder, said annular member, and said elongate member;

engaging said cylinder with an external bodily surface between said nose and said upper lip;

applying said pressure to said annular member and transferring said pressure to said cylinder;

compressing an area of nasal vascularization between said nose and said upper lip with said pressure transferred to said cylinder; and attenuating said nosebleed.

12. The method of claim 11, wherein said compressing said area of nasal vascularization comprises compressing a portion of a superior labial artery.

13. The method of claim 12, wherein said compressing said portion of said superior labial artery comprises compressing a septal branch of said superior labial artery.

14. The method of claim 13, wherein said compressing said septal branch of said superior labial artery comprises constricting said septal branch of said superior labial artery to attenuate said nosebleed.

* * * * *